US010076613B2

(12) United States Patent
Patton et al.

(10) Patent No.: US 10,076,613 B2
(45) Date of Patent: *Sep. 18, 2018

(54) PRESERVATIVE FREE INSULIN FORMULATIONS

(71) Applicant: Dance Biopharm Inc., Brisbane, CA (US)

(72) Inventors: John S. Patton, San Francisco, CA (US); Ryan S. Patton, San Francisco, CA (US); Mei-chang Kuo, Palo Alto, CA (US); Yehuda Ivri, Newport Beach, CA (US)

(73) Assignee: Dance Biopharm Inc., Brisbane, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/878,951

(22) Filed: Oct. 8, 2015

(65) Prior Publication Data

US 2016/0129088 A1    May 12, 2016

Related U.S. Application Data

(63) Continuation of application No. 13/004,645, filed on Jan. 11, 2011, now Pat. No. 9,180,261.

(Continued)

(51) Int. Cl.
*A61M 15/00* (2006.01)
*A61M 11/00* (2006.01)
(Continued)

(52) U.S. Cl.
CPC ....... *A61M 15/0028* (2013.01); *A61K 9/0073* (2013.01); *A61K 9/122* (2013.01);
(Continued)

(58) Field of Classification Search
CPC .. A61M 11/00; A61M 11/001; A61M 11/005; A61M 15/00; A61M 15/001;
(Continued)

(56) References Cited

U.S. PATENT DOCUMENTS

| 4,564,129 A | 1/1986 | Urban et al. |
| 5,164,740 A | 11/1992 | Ivri |

(Continued)

FOREIGN PATENT DOCUMENTS

| CN | 2461580 Y | 11/2001 |
| EP | 2514412 | 10/2012 |

(Continued)

OTHER PUBLICATIONS

International Search Report and Written Opinion of PCT/US2011/020925 dated Mar. 14, 2011, all pages.

(Continued)

*Primary Examiner* — Rachel T Sippel
(74) *Attorney, Agent, or Firm* — Kilpatrick Townsend & Stockton LLP

(57) ABSTRACT

One embodiment describes an insulin formulation that is specifically adapted for aerosolization. The formulation includes a major amount of water and a minor amount of insulin. Further, the formulation is preservative free, without meta-cresol, cresol or phenol, to permit the formulation to be aerosolized using a vibrating aperture plate without substantial foaming of the insulin formulation.

11 Claims, 5 Drawing Sheets

Related U.S. Application Data

(60) Provisional application No. 61/335,769, filed on Jan. 12, 2010.

(51) Int. Cl.
    *A61K 38/20* (2006.01)
    *A61K 9/00* (2006.01)
    *A61K 38/28* (2006.01)
    *A61K 9/12* (2006.01)
    *A61K 33/30* (2006.01)
    *A61M 16/00* (2006.01)

(52) U.S. Cl.
CPC .............. *A61K 33/30* (2013.01); *A61K 38/28* (2013.01); *A61M 11/00* (2013.01); *A61M 11/001* (2014.02); *A61M 11/005* (2013.01); *A61M 15/009* (2013.01); *A61M 15/0021* (2014.02); *A61M 15/0065* (2013.01); *A61M 15/0085* (2013.01); *A61M 15/0091* (2013.01); *A61M 2016/0021* (2013.01); *A61M 2016/0039* (2013.01); *A61M 2202/0468* (2013.01); *A61M 2205/3334* (2013.01); *A61M 2205/583* (2013.01); *A61M 2205/587* (2013.01)

(58) Field of Classification Search
CPC .... A61M 15/0085; B05B 17/00; B05B 17/06; B05B 17/0607; B05B 17/0615; B05B 17/0623; B05B 17/063; B05B 17/0638; B05B 17/0646; B05B 17/0669
See application file for complete search history.

(56) References Cited

U.S. PATENT DOCUMENTS

| | | | |
|---|---|---|---|
| 5,261,601 A | 11/1993 | Ross et al. | |
| 5,586,550 A | 12/1996 | Ivri et al. | |
| 5,758,637 A | 6/1998 | Ivri et al. | |
| 5,915,378 A | 6/1999 | Lloyd et al. | |
| 5,938,117 A | 8/1999 | Ivri | |
| 6,014,970 A | 1/2000 | Ivri et al. | |
| 6,085,740 A | 7/2000 | Ivri et al. | |
| 6,131,567 A | 10/2000 | Gonda et al. | |
| 6,205,999 B1 | 3/2001 | Ivri et al. | |
| 6,211,144 B1 | 4/2001 | Havelund | |
| 6,312,665 B1 | 11/2001 | Modi | |
| 6,427,682 B1 | 8/2002 | Klimowicz et al. | |
| 6,467,476 B1 | 10/2002 | Ivri et al. | |
| 6,489,292 B1 | 12/2002 | Havelund et al. | |
| 6,540,153 B1 | 4/2003 | Ivri | |
| 6,540,154 B1 | 4/2003 | Ivri et al. | |
| 6,629,646 B1 | 10/2003 | Ivri | |
| 6,635,617 B1 | 10/2003 | Havelund | |
| 6,640,804 B2 | 11/2003 | Ivri et al. | |
| 6,755,189 B2 | 6/2004 | Ivri et al. | |
| 6,814,071 B2 | 11/2004 | Klimowicz et al. | |
| 6,921,020 B2 | 7/2005 | Ivri | |
| 6,926,208 B2 | 8/2005 | Ivri | |
| 6,978,941 B2 | 12/2005 | Litherland et al. | |
| 7,032,590 B2 | 4/2006 | Loeffler et al. | |
| 7,040,549 B2 | 5/2006 | Ivri et al. | |
| 7,066,398 B2 | 6/2006 | Borland et al. | |
| 7,083,112 B2 | 8/2006 | Ivri | |
| 7,100,600 B2 | 9/2006 | Loeffler et al. | |
| 7,108,197 B2 | 9/2006 | Ivri | |
| 7,174,888 B2 | 2/2007 | Ivri et al. | |
| 7,195,011 B2 | 3/2007 | Loeffler et al. | |
| 7,387,996 B2 | 6/2008 | Langkjaer | |
| 7,628,339 B2 | 12/2009 | Ivri et al. | |
| 9,180,261 B2 | 11/2015 | Patton et al. | |
| 2001/0037805 A1 | 11/2001 | Gonda et al. | |
| 2003/0072740 A1 | 4/2003 | Milstein et al. | |
| 2004/0045546 A1* | 3/2004 | Hirsh ................... | A61K 9/0078 128/200.14 |
| 2004/0134494 A1 | 7/2004 | Papania et al. | |
| 2006/0239930 A1 | 10/2006 | Lamche et al. | |
| 2007/0163572 A1 | 7/2007 | Addington et al. | |
| 2008/0029083 A1 | 2/2008 | Masada et al. | |
| 2008/0233053 A1 | 9/2008 | Gross et al. | |
| 2009/0099065 A1 | 4/2009 | Madsen et al. | |
| 2009/0157037 A1 | 6/2009 | Iyer et al. | |
| 2009/0236445 A1* | 9/2009 | Lintern ................... | A61M 11/00 239/483 |
| 2011/0017431 A1 | 1/2011 | Yang et al. | |
| 2011/0168170 A1 | 7/2011 | Patton et al. | |
| 2011/0168172 A1 | 7/2011 | Patton et al. | |
| 2013/0269684 A1 | 10/2013 | Patton | |
| 2013/0269694 A1 | 10/2013 | Patton et al. | |
| 2014/0135682 A1 | 5/2014 | Frost et al. | |
| 2014/0328943 A1 | 11/2014 | Havelund et al. | |
| 2015/0352297 A1 | 12/2015 | Stedman et al. | |
| 2015/0352301 A1 | 12/2015 | Stedman et al. | |
| 2016/0001018 A1 | 1/2016 | Fink et al. | |
| 2016/0001019 A1 | 1/2016 | Fink et al. | |
| 2016/0129088 A1 | 5/2016 | Patton et al. | |
| 2016/0243199 A1 | 8/2016 | Bueche et al. | |

FOREIGN PATENT DOCUMENTS

| | | |
|---|---|---|
| WO | 1995/24183 A1 | 9/1995 |
| WO | 2000029013 | 5/2000 |
| WO | 03/030829 A2 | 4/2003 |
| WO | 2007/047948 A2 | 4/2007 |
| WO | 2009/111612 A1 | 9/2009 |
| WO | 2011088071 | 7/2011 |
| WO | 2016137569 | 9/2016 |

OTHER PUBLICATIONS

Sélam, J.-L., *Inhaled Insulin: Promises and Concerns*, Journal of Diabetes Science and Technology 2(2):311-315 (Mar. 2008).

*Aradigm and Novo Nordisk Execute Further Restructuring of Partnership*, Aradigm Press Release (Jul. 5, 2006), http://investor.aradigm.com/releasedetail.cfm?ReleaseID=325263.

*Aradigm Regains Inhaled Insulin Program from Novo Nordisk*, GEN News Highlight (Oct. 9, 2008), http://www.genengnews.com/gen-news-highlights/aradigm-regains-inhaled-insulin-program-from-novo-nordisk/43253230/?kwrd=Aradigm.

*Novo Nordisk Assigns Inhaled Insulin Patent Portfolio to Aradigm Corporation*, Fierce Biotech (Oct. 9, 2008), http://www.fiercebiotech.com/press-releases/novo-nordisk-assigns-inhaled-insulin-patent-portfolio-aradigm-corporation.

Novo Nordisk refocuses its activities within inhaled insulin and discontinues the development of AERx, Fierce Biotech (Jan. 14, 2008), http://www.fiercebiotech.com/press-releases/novo-nordisk-refocuses-its-activities-within-inhaled-insulin-and-discontinues-develop.

Russian Patent Application No. 2012134402, Office Action dated Jun. 10, 2014.

Liu, F., et al., "Pulmonary Delivery of Free and Liposomal Insulin," Pharmaceutical Research, vol. 10, 1993, 5 pages.

Extended European Search Report from corresponding European Application No. 11733287.4, dated Jul. 12, 2013, 6 pages.

European Search Report of EP 11733287 dated Jul. 12, 2013, 12 pages.

Liu, F-Y, "Pulmonary Delivery of Free Liposomal Insulin," Pharmaceutical Research, Kluwer Academic Publishers, New York, NY, vol. 10, No. 2, Feb. 1, 1993, 5 pages.

U.S. Appl. No. 13/004,645, Final Office Action dated Sep. 20, 2013, 17 pages.

U.S. Appl. No. 13/004,645, Final Office Action dated Apr. 29, 2014, 21 pages.

U.S. Appl. No. 13/004,645, Final Office Action dated Mar. 10, 2015, 24 pages.

U.S. Appl. No. 13/004,645, Non Final Office action dated Nov. 25, 2013, 19 pages.

U.S. Appl. No. 13/004,645, Non Final Office Action dated Mar. 13, 2013, 15 pages.

(56) References Cited

OTHER PUBLICATIONS

U.S. Appl. No. 13/004,645, Notice of Allowance dated Jul. 8, 2015, 11 pages.
U.S. Appl. No. 14/977,137, Non-Final Office Action dated Jun. 29, 2017, 9 pages.
International Patent Application No. PCT/US2011/020926, International Search Report and Written Opinion, dated Mar. 14, 2011, 10 pages.
International Patent Application No. PCT/US2015/067129, International Search Report and Written Opinion, dated Feb. 26, 2016, 7 pages.
International Patent Application No. PCT/US2015/067129, International Preliminary Report on Patentability, dated Aug. 29, 2017, 6 pages.
Berchtold H. and Hilgenfeld R., 1999, "Binding of Phenol to R6 Insulin Hexamers," *Biopolymers* 51(2):165-172.
Brange J. et al., 1992, "Chemical stability of insulin: 1. Hydrolytic degradation during storage of pharmaceutical preparations," *Pharm. Res.* 9:715-726.
Brange J., et al., 1992, "Chemical stability of insulin: 2. Formation of higher molecular weight transformation products during storage of pharmaceutical insulin preparations," *Pharm. Res.* 9: 149-158.
Brange J., and Langkjaer L., 1992, "Chemical stability of insulin: 3. Influence of excipients, formulation, and pH," *Acta Pharm. Nord.* 4:149-158.
Brange J, 1992, "Chemical stability of insulin: 4. Kinetics and mechanisms of the chemical transformation in pharmaceutical formulation," *Acta Pharm. Nord.* 4:209-222.
Brange J. et al., 1992, "Chemical stability of insulin:5. Isolation, characterization and identification of insulin transformation products," *Acta Pharm. Nord.* 4:223-232.
Brange, et al. (1994) Stability of insulin: studies on the physical and chemical stability of insulin in pharmaceutical formulation (Kluwer Academic Publishers; Dordrecht, The Netherlands).
Brange and Havelund (1983) Properties of Insulin in Solution, In: Artificial Systems for Insulin Delivery (Brunetti, et al. eds., Raven Press, New York), pp. 83-88.
Brzovic, et al., 1994, "Structural Asymmetry and Half-Site Reactivity in the T to R Allosteric Transition of the Insulin Hexamer," *Biochemistry* 33(44):13057-13069.
Darrington, et al., 1994, "The Role of Intramolecular Nucleophilic Catalysis and the Effects of Self-Association on the Deamidation of Human Insulin at Low pH," *Pharm. Res.* 11(6):784-793.
Derewenda, et al., 1989, "Phenol stabilizes more helix in a new symmetrical zinc insulin hexamer," *Nature* 338 (6216): 594-596.
Derewenda, et al., 1989, "Molecular structure of insulin: the insulin monomer and its assembly," *British Medical Bulletin* 45(1):4-18.
European Pharmacopeia: Insulin Human (01/2005:0838, 1800-0801), Acta. Pharm. Nord. 223-232.
Galloway, et al., 1981, "Factors Influencing the Absorption, Serum Insulin Concentration, and Blood Glucose Responses After Injections of Regular Insulin and Various Insulin Mixtures," *Diabetes Care* 4(3):366-376.
Kim, et al., 1992, "pH Dependent Conformational Changes in the T- and R-States of Insulin in Solution: Circular Dichroic Studies in the pH Range of 6 to 10," *Biochemical and Biophysical Research Communications* 186(2):1115-1120.
Profit, Louise, 2005, "Exubera® (inhaled insulin): an evidence-based review of its effectiveness in the management of diabetes," *Core Medical Publishing*, Knutsford, UK, 1(2): pp. 89-101.
Sluzky et al., 1992, "Mechanism of Insulin Aggregation and Stabilization in Agitated Aqueous Solutions," *Biotechnol. Bioeng.* 40:895-903.
Strickley, et al., 1997, "Solid-State Stability of Human Insulin II. Effects of Water on Reactive Intermediate Partitioning in Lyophiles from pH 2-5 Solutions: Stabilization against Covalent Dimer Formation," *Journal of Pharmaceutical Sciences* 86(6): 645-53.

\* cited by examiner

FIG.3

SECONDS REQUIRED TO NEBULIZE 100 UL

Legend:
- LANTUS
- HUMALOG
- EX #3  200
- EX #2  400
- EX #1  800

REMAINDER LEFT IN DEVICE

| | |
|---|---|
| LANTUS | 6.9 UL |
| HUMALOG | 2.8 UL |
| EXAMPLE 3 200IU | 1.4 UL |
| EXAMPLE 2 400IU | 2.7 UL |
| EXAMPLE 1 800IU | 2.2 UL |

PRESERVATIVE FREE INSULIN FORMULATIONS

CROSS-REFERENCES TO RELATED APPLICATIONS

This application is a continuation of U.S. patent application Ser. No. 13/004,645, filed on Jan. 11, 2011, which is a continuation in part application and claims the benefit of U.S. Provisional Application No. 61/335,769, filed on Jan. 12, 2010, the complete disclosure of which is herein incorporated by reference.

This application is also related to copending U.S. application Ser. No. 13/004,662, entitled "PRESERVATIVE-FREE SINGLE DOSE INHALER SYSTEMS" and filed on the same date as the present application, the complete disclosure of which is herein incorporated by reference.

BACKGROUND OF THE INVENTION

This application relates generally to the field of insulin formulations, and in particular to insulin formulations that can be aerosolized using an aerosolizer that vibrates a mesh at high frequencies.

A variety of insulin formulations have been widely available for years. These formulations are primarily engineered to have a long shelf life and are typically administered by injection. This application relates to insulin formulations that are particularly suited for delivery by inhalation as an aerosolized spray.

BRIEF SUMMARY OF THE INVENTION

In one embodiment, an insulin formulation is provided that is specifically adapted for aerosolization. The formulation comprises a major amount of water and a minor amount of insulin. Further, the formulation is preservative free to permit the formulation to be aerosolized using a vibrating aperture plate without substantial foaming of the insulin formulation. For example, the formulation does not include meta-cresol, cresol, phenol or the like.

In one aspect, the insulin has a concentration of about 100 IU/ml to about 1200 IU/ml, and more preferably from about 200 IU/ml to about 800 IU/ml of human insulin. Also, the water may comprise in volume about 99.8% to about 97.0%, and the human insulin may comprise in volume about 0.2% to about 3.0%.

In another embodiment, an insulin formulation is provided that is specifically adapted for aerosolization. The formulation consists essentially of a major amount of water and minor amounts of insulin, HCl, and NaOH. The formulation is preservative free such that the formulation may be aerosolized using a vibrating aperture plate without substantial foaming of the formulation.

In one aspect, the insulin has a concentration of about 100 IU/ml to about 1200 IU/ml, and more preferably from about 200 IU/ml to about 800 IU/ml of human insulin. Also, the water may comprise in volume about 99.8% to about 97.0%, the human insulin comprises in volume about 0.2% to about 3.0%.

In still another embodiment, the invention provides an insulin formulation specifically adapted for aerosolization that comprises a major amount of water and a minor amount of insulin. The formulation is capable of being aerosolized as a spray using a vibrating aperture plate having a plurality of apertures that vibrates at a frequency in the range from about 50 kHz to about 150 kHz. Also, the amount of the insulin formulation has a volume of up to about 200 uL, and the time to aerosolize 97% is less than about 22 seconds.

In a particular aspect, the insulin formulation does not contain a preservative such that the formulation may be aerosolized using the vibrating aperture plate without substantial foaming of the formulation. Further, the insulin may have a concentration of about 100 IU/ml to about 1200 IU/ml, and more preferably from about 200 IU/ml to about 800 IU/ml of human insulin.

The invention in one embodiment also provides an exemplary method for aerosolizing an insulin formulation. The method includes the use of an insulin formulation comprising a major amount of water and minor amounts of insulin, HCl and NaOH. An amount of the insulin formulation is supplied to a rear side of an aperture plate having a plurality of apertures. The aperture plate is vibrated while the insulin formulation is at the rear side. Vibration causes the supplied insulin to be ejected from a front side of the aperture plate as an aerosolized spray without substantial foaming of the insulin formulation.

In one step, at least about 97% of the formulation is ejected. Also, the amount of the insulin formulation has a volume of up to about 100 µL, and the time to aerosolize the at least about 97% is less than about 11 seconds. In another aspect, the aperture plate is vibrated with an amplitude that is less than about 4 µm, in some cases less than about 3 µm, and in further cases less than about 2 µm. Further, the aerosolized spray may comprise aerosolized droplets having a mean size in the range from about 3 µm to about 8 µm, and preferably from about 3 µm to about 6 µm. In another aspect, the formulation has less than about 3%, in some cases less than about 1%, and more preferably less than about 0.1% converted to foam when vibrating the aperture plate.

In a certain aspect, the insulin has a concentration of about 200 IU/ml to about 800 IU/ml of human insulin. Also, the aperture plate may have a diameter in the range from about 5 mm to about 8 mm, with apertures having a size in the range from about 3 µm to about 8 µm, a thickness in the range from about 50 microns to about 70 microns, and is vibrated at a frequency in the range from about 50 kHz to about 150 kHz.

In still a further embodiment, the invention provides an aerosolization system that comprises an inhaler comprising a housing defining a mouthpiece, and an aerosol generator disposed in the housing. The aerosol generator comprises a vibratable membrane having a front face and a rear face, and a vibratable element used to vibrate the membrane. The system further includes a container containing a volume of an insulin formulation consisting essentially of a major amount of water and a minor amount of insulin. The formulation is preservative free such that the formulation may be aerosolized using a vibrating aperture plate without substantial foaming of the formulation.

In one aspect, the insulin has a concentration of about 200 IU/ml to about 800 IU/ml of human insulin. In a further aspect, the aperture plate has apertures having a size in the range from about 3 µm to about 8 µm. Further, the vibratable membrane may be configured to vibrate with a frequency that is less than about 2 µm.

BRIEF DESCRIPTION OF THE DRAWINGS

FIG. 3 is a graph illustrating the time required to aerosolize different insulin formulations.

DETAILED DESCRIPTION OF THE INVENTION

Figure 1:
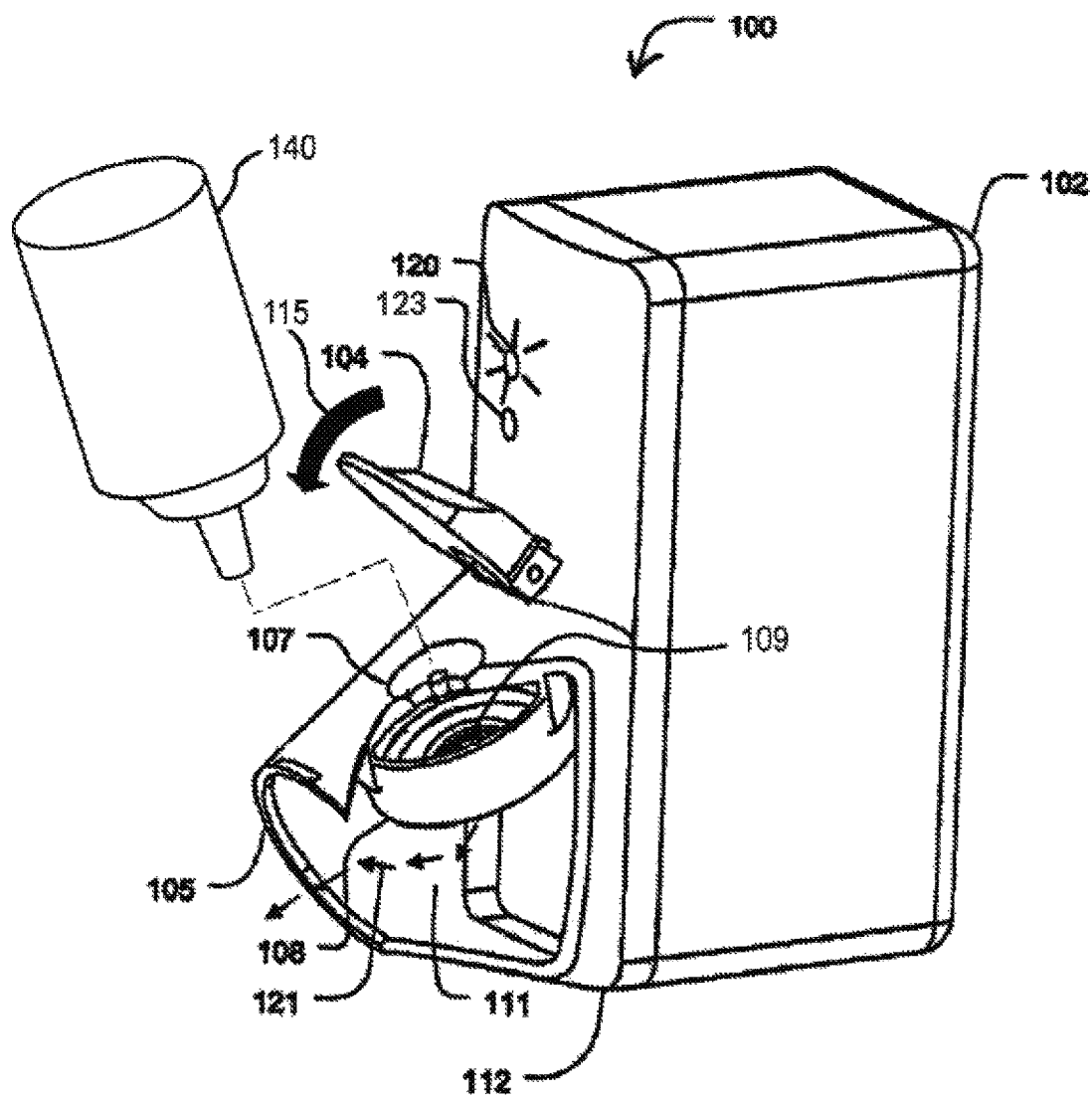
FIG. 1 is a perspective, partial cut-away view of one embodiment of a dispensing apparatus according to the invention.

Certain embodiments of the invention provide a preservative free insulin formulation that may be used with an aerosolization device to provide an aerosolized spray of insulin. More specifically, the insulin formulations do not contain any preservatives, including phenol, metacresol, chloro-cresol, thymol and mixtures thereof or the like. The absence of such preservatives enable the formulations to be aerosolized as a liquid spray using a vibrating mesh or aperture plate that operates at high frequencies. The absence of such preservatives permits a dosage of the formulation to come into contact with the vibrating mesh without substantial foaming of the formulation. In turn, the formulation may be aerosolized more quickly. Further, substantially all of the liquid is able to be aerosolized.

The formulations contain water in major and human insulin in minor amount. The formulations may also include various concentrations of human insulin. For example, the concentrations may be in the range from about 100 IU insulin/ml of formulation to about 1200 IU insulin/ml of formulation, and more preferably from about 200 IU insulin/ml of formulation to about 800 IU insulin/ml of formulation.

In addition to water and human insulin, the formulations may also include zinc, acetate, chloride and sodium. The zinc ion and acetate ion come from the drug substance, e.g., the insulin. The chloride ion and sodium ion are added during dissolution of the insulin and adjustment of the pH. Merely by way of example, the NaCl concentration may be about 20 mM for an 800 IU insulin/ml formulation, about 10 mM for a 400 IU insulin/ml formulation, and about 5 mM for a 200 IU insulin/ml formulation.

The following are various non-limiting examples of preservative free formulations that may be used according to the invention:

EXAMPLE 1

800IU Insulin/ml Formulation

In this example, 50 ml of the 800 IU insulin solution was made by suspending 1400 mg human insulin (with 2 to 4 $Zn^{2+}$ per insulin hexamer) in 44 ml water, then dissolved the insulin by adding 1.0 ml 1N HCl to pH about 3.0. After all of the insulin dissolved, 1.6 ml 1N NaOH was slowly added to titrate the insulin solution to pH 7.4. Finally, water was added to 50 ml.

EXAMPLE 2

400 IU Insulin/ml Formulation

In this second example, 50 ml of the 400 IU insulin solution was made by suspending 700 mg human insulin (with 2 to 4 $Zn^{2+}$ per insulin hexamer) in 44 ml water, then dissolved the insulin by adding 0.5 ml 1N HCl to pH about 3.0. After all of the insulin dissolved, about 0.8 ml 1N NaOH was slowly added to titrate the insulin solution to pH 7.4. Finally, water was added to 50 ml.

EXAMPLE 3

200 IU Insulin/ml Formulation

In this third example, 50 ml of the 200 IU insulin solution was made by suspending 350 mg human insulin (with 2 to 4 $Zn^{2+}$ per insulin hexamer) in 44 ml water, then dissolved the insulin by adding 0.25 ml 1N HCl to pH about 3.0. After all of the insulin dissolved, about 0.4 ml 1N NaOH was slowly added to titrate the insulin solution to pH 7.4. Finally, water was added to 50 ml.

A wide variety of inhalers or aerosolizers may be used to aerosolize the preservative free solution. For example, an aerosolizing apparatus may comprise a housing defining a dispensing outlet, a vibratable membrane having a front face exposed at the outlet and a rear face for receiving a liquid to be dispensed, and a vibrating mechanism connected to the housing and operable to vibrate the membrane to dispense aerosol of the liquid through the membrane. In some cases, a liquid delivery system may also be used to deliver a metered quantity of the liquid from to the rear face of the membrane. In this way, a metered quantity of liquid is dispensable at the outlet by operating the vibrating mechanism for an operating period sufficient to completely aerosolize the metered quantity of the rear face.

Examples of certain types of aerosolizers that may be used are described in copending U.S. application Ser. No. 13/004,662, entitled "PRESERVATIVE-FREE SINGLE DOSE INHALER SYSTEMS" and filed on the same date as the present application, previously incorporated by reference.

Referring now to FIG. 1, one embodiment of an inhaler will be described. FIG. 1 illustrates a partially cut-away view of an inhaler 100. Inhaler 100 may be used in connection with various containers that supply the liquid insulin. For example, inhaler 100 may be used with a unit dose blister package for supplying a metered quantity of insulin to the inhaler. Inhaler 100 comprises two subassemblies 102 and 112. The first subassembly 102 defines a compartment for the electronic circuitry and the batteries, and the second subassembly 112 defines a housing with a dispensing outlet 105 and contains a vibratable membrane aerosol generator 108 and a lid 104 that may be closed as shown by arrow 115. Aerosol generator 108 has a front face exposed at the outlet duct 111 and a rear face 109 contacted in use by liquid to be dispensed. Aerosol generator 108 is connected to the housing of subassembly 112 and is operable to dispense the active pharmaceutical agent as an aerosol through the mouthpiece 105. Exemplary aerosol generators that may be used are also described in U.S. Pat. Nos. 5,164,740; 6,629,646; 6,926,208; 7,108,197; 5,938,117; 6,540,153; 6,540,154; 7,040,549; 6,921,020; 7,083,112; 7,628,339; 5,586,550; 5,758,637; 6,085,740; 6,467,476; 6,640,804; 7,174,888; 6,014,970; 6,205,999; 6,755,189; 6,427,682; 6,814,071; 7,066,398; 6,978,941; 7,100,600; 7,032,590; 7,19,5011, incorporated herein by reference. These references describe exemplary aerosol generators, ways to manufacture such aerosol generators and ways to supply liquid to aerosol generators, and are incorporated by reference for at least these features. The aerosol generators may comprise vibratable membranes having tapered aperture with a size in the range from about 3 μm to about 8 μm, preferably from about 3 μm to about 6 μm, and in some cases around 4 μm. The membrane may be domed shaped and be vibrated by an annular piezoelectric element that circumscribes the apertures. The diameter of the membrane may be in the range from about 5 mm to about 8 mm. The membrane may also have a thickness in the range from about 50 microns to about 70 microns. Typically, the membrane will be vibrated at a frequency in the range from about 50 kHz to about 150 kHz.

Further, to minimize foaming of the insulin formulations, the membrane may be vibrated at an amplitude that is less than about 4 µm, preferably less than 3 µm and more preferably less than 2 µm.

Each time a metered quantity of liquid is supplied to inhaler 100, it is delivered to the rear face 109 of the aerosol generator. Hence, for each use a metered quantity of aerosolized pharmaceutical agent may be dispensed at the mouthpiece outlet 105 by operation of the aerosol generator.

Inhaler 100 further includes a well 107 to receive the content of a container so that it may be supplied to the aerosol generator 108. The well 107 has a concave shape and defines a fluid passage to the vibrating aerosol generator 108.

Figure 2:
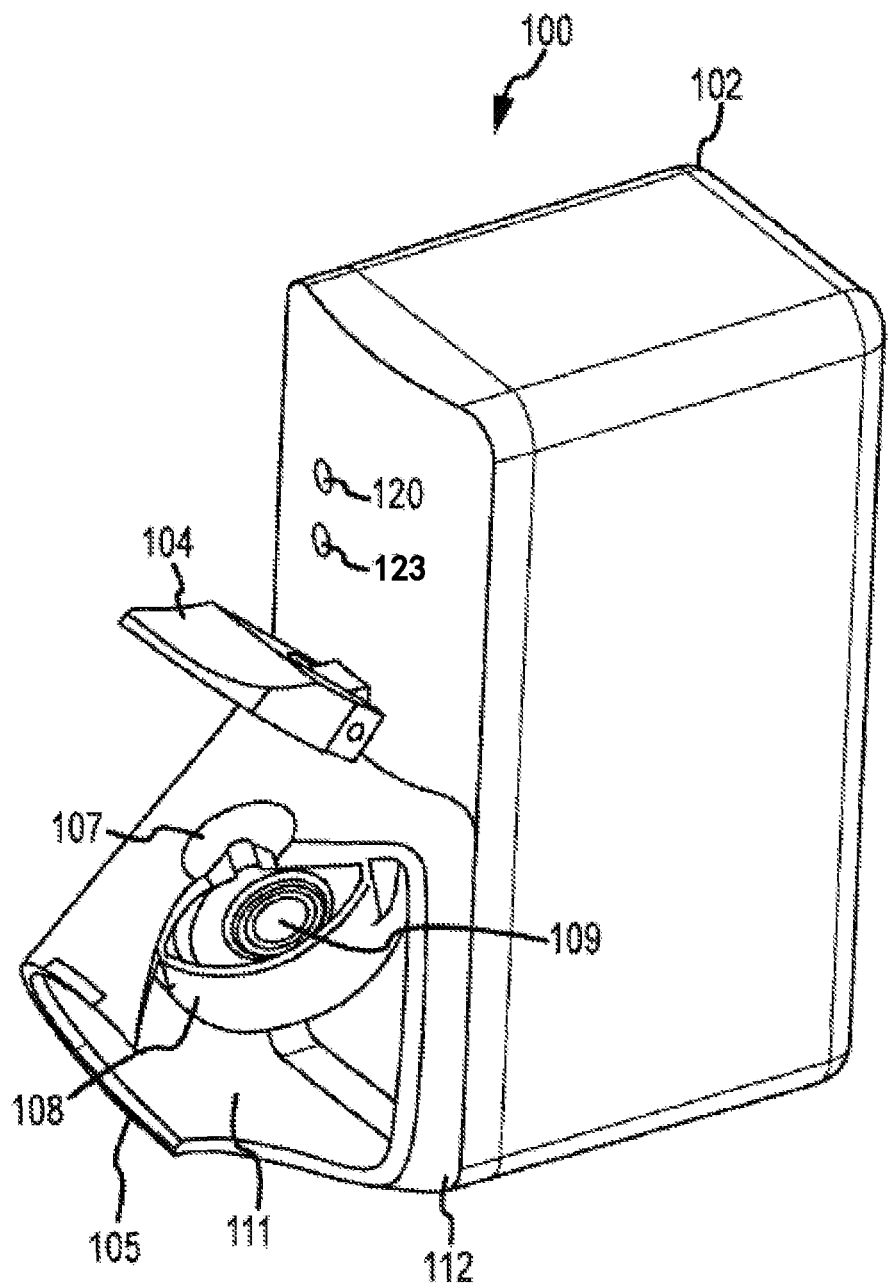
FIG. 2 is a more detailed view of the dispensing apparatus of FIG. 1.

FIG. 2 illustrates the vibrating membrane 109 of the aerosol generator 108 in greater detail. When a volume of liquid is dispensed an indicator light 120 starts to blink signaling to the patient that the inhaler 100 is ready for use. At any time shortly thereafter the patient may inhale through the mouthpiece 105. Patient inhalation is detected by a flow sensor which in turn activates the aerosol generator 108 to produce aerosol particles into the duct 111. Aerosol is entrained in the inhalation air flow in the direction shown by arrows 121 and flow via the respiratory system to the lungs of the patient. When the entire dose is aerosolized, which may take one or more breaths, the "end-of-dose" indicator light 123 lights a second time to signal the patient that the entire dose has been delivered. Delivery of the entire dose is obtained when at least about 95% of the dose is delivered, more preferably 98% and most preferably when more than 99% of the dose is delivered. In one embodiment, the opening funnel to the aerosol generator is sufficiently large such that the liquid delivery to the aerosol generator is delivered in its entirety. To receive the dose, the patient may take several inhalations or a single inhalation depending on the volume delivered to the mesh and the patient's breathing capacity. Each inhalation should be a deep breath to assure that the aerosol reaches deeply to the lungs.

The preservative-free insulin formulations are particularly useful in that they do not have substantial foaming when coming into contact with the vibrating membrane. In turn, this permits the formulation to be rapidly aerosolized. This is a critical feature in that the dosage needs to be quickly aerosolized so that the user can inhale the insulin in a short time frame. In most cases, it is desirable to limit the number of inhalations required to administer the formulation. Depending on the user's ability to inhale, it is desirable to administer the entire dosage in about 1 to 3 breaths. Typical dosage amounts are in the range from about 40 µL to about 200 µL. Aerosolizing these volumes fast enough to permit them to be inhaled within a few breaths is a critical feature of the invention. It is desirable to aerosolize these volumes in less than about 22 seconds, and more particularly less than about 15 seconds to permit them to be inhaled in about 1 to 3 breaths.

Figure 4:
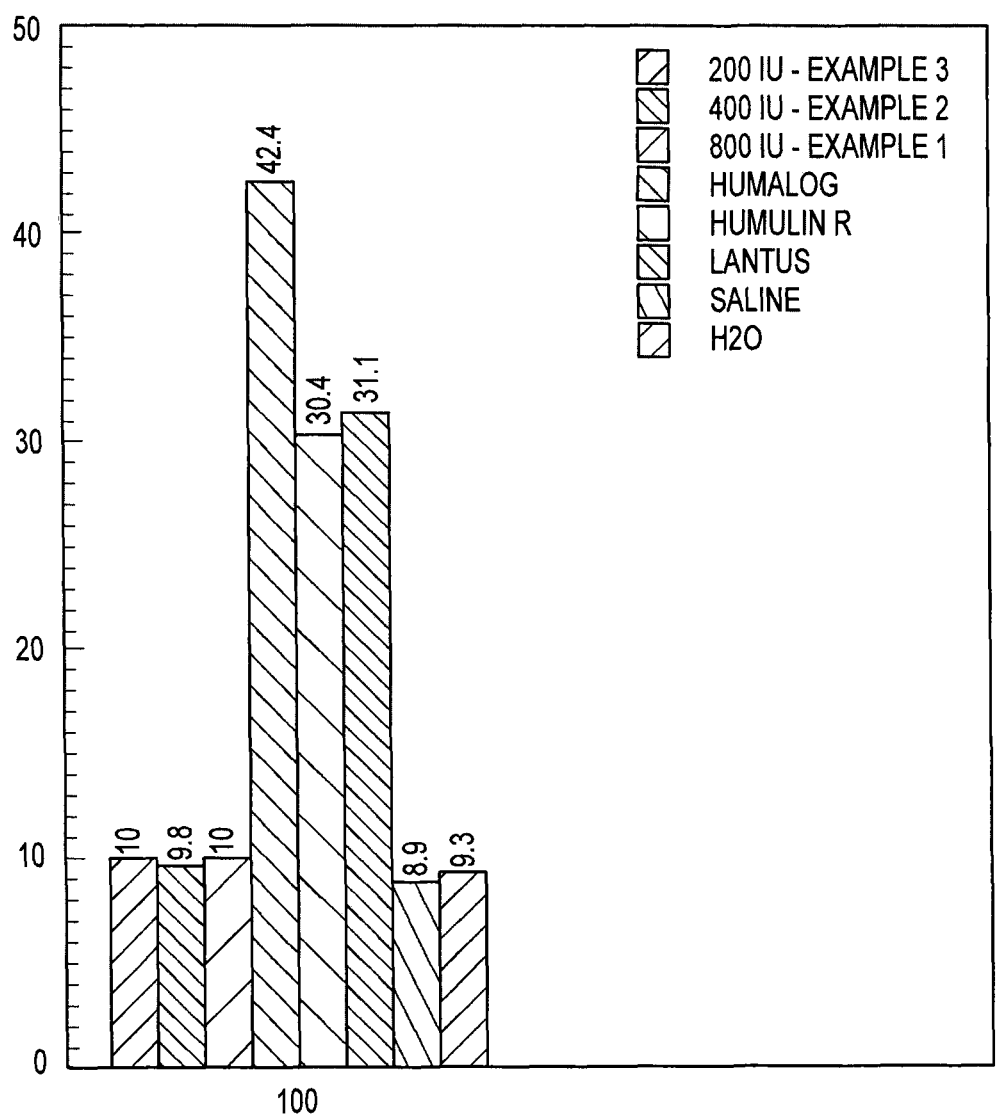
FIG. 4 is a graph illustrating aerosolization times for various insulin formulations as well as for water and saline.

The graphs of FIGS. 3 and 4 illustrate how the insulin formulations of the invention provide this critical feature while commercially available insulin formulations are unable to aerosolize in an acceptable time frame. As shown, the Humalin, Lantus and Humalog formulations took in excess of 30 seconds to aerosolize 100 µL of insulin formulation. This is because both of these formulations had significant foaming that prevented the formulation from being ejected as liquid droplets from the front face of the vibrating membrane. Further, with the Lantus formulation, 6.9 µL remained at the end of the test. Preferably, substantially all the liquid will be aerosolized, and typically less than about 3 µL will remain, corresponding to an aerosolization efficiency of at least about 97% aerosolization.

In contrast to the insulin formulations that contain preservatives, the insulin formulations of the invention (with concentrations of 200 IU, 400 IU and 800 IU, corresponding to Examples 3, 2, and 1, respectively) were each aerosolized in about 10 seconds. With less than 3 ul of formulation remaining, more than about 97% of the formulation was aerosolized. By aerosolizing this volume in around 10 seconds, most individuals, including children, are able to inhale the complete dosage in around 1 to 3 breaths. The insulation formulations of the invention were able to aerosolize at essentially the same rate as water and a saline solution.

One significant reason for the foaming is due to the preservative used in the formulation. For example, many formulations contain the preservative meta-cresol at 2.5-3.15 mgs/ml. However this additive was found to have no effect on foaming FIG. 4. Thus, eliminating such preservatives substantially eliminates foaming and markedly increases aerosolization times.

As one specific example, each milliliter of HUMALOG contains 100 iu lispro, 16 mg glycerin, 1.88 mg dibasic sodium phosphate, 3.15 mg meta-cresol, zinc oxide content adjusted to provide 0.0197 mg zinc ion, trace amounts of phenol, and water for injection. Insulin lispro has a pH of 7.0-7.8, and hydrochloric acid (10%) and/or sodium hydroxide (10%) may be added to adjust pH.

As another example, LANTUS consists of insulin glargine dissolved in a clear aqueous fluid. Each milliliter of LANTUS (insulin glargine injection) contains 100 IU (3.6378 mg) insulin glargine. Inactive ingredients for the 10 mL vial are 30 mcg zinc, 2.7 mg m-cresol, 20 mg glycerol 85%, 20 mcg polysorbate 20, and water for injection. Inactive ingredients for the 3 mL cartridge are 30 mcg zinc, 2.7 mg m-cresol, 20 mg glycerol 85%, and water for injection. The pH is adjusted by addition of aqueous solutions of hydrochloric acid and sodium hydroxide. LANTUS has a pH of approximately 4.

Further, each milliliter of Humulin contains 500 IU of human insulin, 16 mg glycerin, 2.5 mg meta-cresol as a preservative, and zinc-oxide calculated to supplement endogenous zinc to obtain a total zinc content of 0.017 mg/100 units. Sodium hydroxide and/or hydrochloric acid may be added during manufacture to adjust pH.

As yet another example, Humalin R formulation is 100 IU recombinant human insulin, 16 mg (174 mM) glycerin, 2.5 mg metacresol (22.7 mM, 0.25%), HCl and NaOH.

Finally Novolin R formulation is 100 IU recombinant human insulin, glycerin, metacresol, HCl and NaOH.

Other formulations containing preservatives are described in U.S. Pat. Nos. 6,489,292 and 6,211,144, incorporated herein by reference. Such preservatives can include phenol, m-cresol, chloro-cresol, thymol and mixtures thereof. Some similar non-phenol preservatives include bi- or tricyclic aliphatic alcohols and purines, such as a bicyclic aliphatic alcohol, including a monoterpenol, such as isopinocampheol, 2,3-pinandiol, myrtanol, borneol, norborneol or fenchol, a tricyclic aliphatic alcohol, such as 1-adamantanol, and a purine, such as adenine, guanine or hypoxanthine. As described in these patents, such preservatives are included to ensure stability of the insulin. However, the preservatives included in the formulations described in these patents cause the formulations to foam when subjected to vibrating aperture plates, significantly increasing the time to aerosolize.

The formulations of the invention do not contain such preservatives or stabilizers. As such, little or no foaming occurs, allowing substantially all of the aerosol generator to rapidly aerosolize the formulations.

Some insulin formulations also include surfactants or detergents. These also can cause foaming in the presence of a vibrating aperture plate or mesh. The formulations of the invention also avoid the use of such surfactants or detergents.

While the formulations of the invention lack the use of preservatives, the integrity of the formulations can still be maintained by proper packaging and management of shelf life. In this way, the formulations may be preservative free and still commercially viable.

Figure 5:
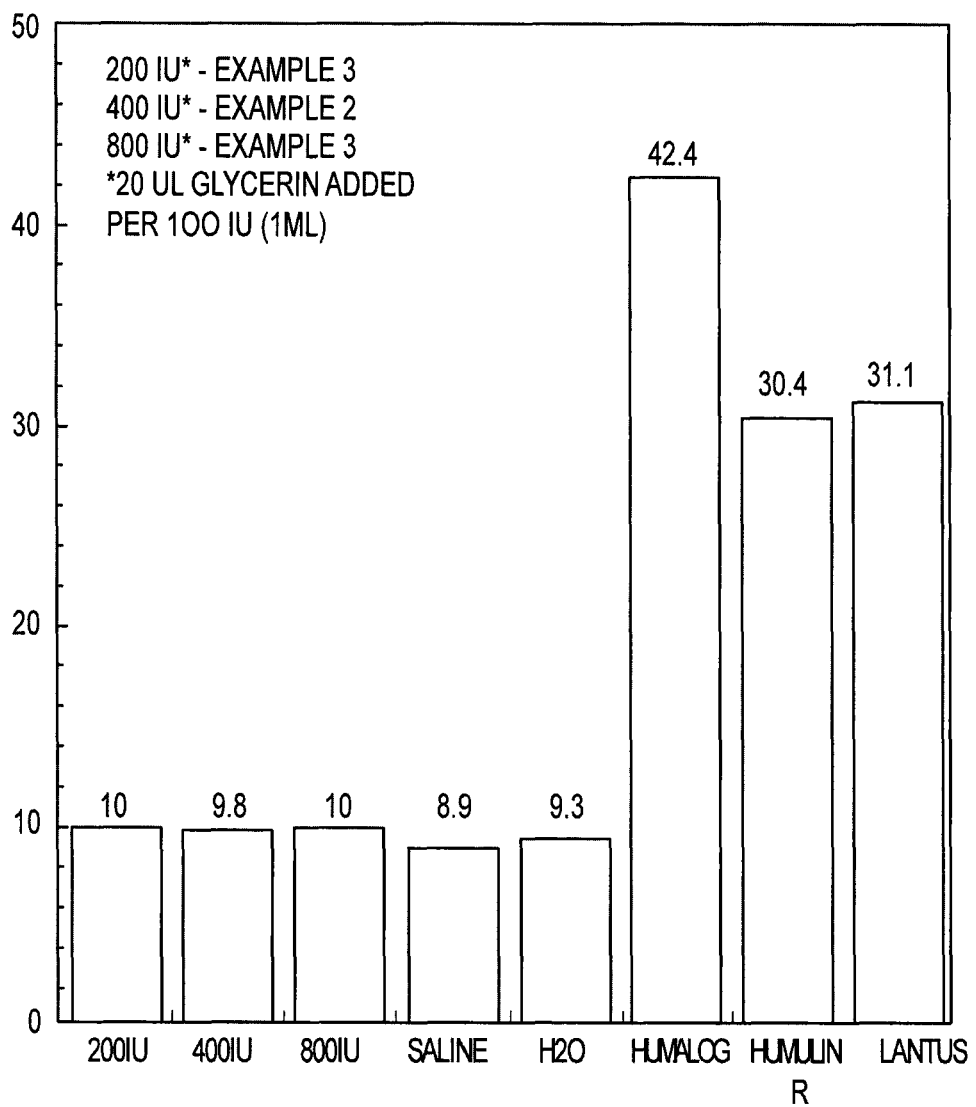
FIG. 5 is a graph illustrating aerosolization times for various insulin formulations, including the formulations of Examples 1-3 when glycol is added.

FIG. 5 illustrates what happens when 20 μL glycol added per 100 IU (1 ml) was added to the formulations of Examples 1-3. These were then compared to Humalin, Lantus and Humalog, saline and water examples of FIG. 4. As shown, inclusion of glycol had essentially no effect on the aerosolization times of Examples 1-3, confirming that glycol does not contribute to foaming, with the main contributor of foaming being the preservatives as previously described.

The invention has now been described in detail for purposes of clarity and understanding. However, it will be appreciated that certain changes and modifications may be practiced within the scope of the appended claims.

What is claimed is:

1. An insulin formulation specifically adapted for aerosolization, the formulation comprising:
    a major amount of water;
    a minor amount of insulin;
    a minor amount of HCl;
    a minor amount of NaOH; and
    2 to 4 $Zn^{2+}$ per insulin hexamer;
    wherein the formulation is preservative free thereby facilitating aerosolization of the formulation as an aerosolized spray using a vibrating aperture plate having a plurality of apertures, and wherein the spray is produced without substantial foaming of the formulation when the formulation is held on a rear face of the aperture plate by gravity and the aerosolized spray exits a front face of the aperture plate solely by vibration of the aperture plate that is vibrated using an annular vibratable element that circumscribes the apertures.

2. An insulin formulation as in claim 1, wherein the insulin has a concentration of about 100 IU/ml to about 1200 IU/ml of human insulin.

3. An insulin formulation as in claim 1, wherein the water comprises in volume about 99.8% to about 97.0%, and the human insulin comprises in volume about 0.2% to about 3.0%.

4. An insulin formulation as in claim 1, wherein the formulation does not include meta-cresol, cresol or phenol.

5. An insulin formulation as in claim 1 wherein the formulation is aerosolized as a spray without substantial foaming when the vibrating aperture plate vibrates at a frequency in the range from about 50 kHz to about 150 kHz, and wherein the amount of the insulin formulation has a volume of up to about 200 μL, and wherein the time to aerosolize at least 97% of the formulation is less than about 22 seconds.

6. An insulin formulation as in claim 1, wherein the insulin formulation does not contain a preservative and thereby is aerosolized without substantial foaming of the formulation.

7. An insulin formulation as in claim 1, wherein the amount of the insulin formulation has a volume of about 40 μL, to about 200 μL.

8. An insulin formulation as in claim 1, wherein the amount of the insulin formulation has a volume of up to about 100 μL, and wherein the time to aerosolize at least 97% of the formulation is less than about 11 seconds.

9. An insulin formulation as in claim 1, wherein the aperture plate is vibrated using the annular vibratable element with an amplitude that is less than about 2 μm.

10. An insulin formulation as in claim 1, wherein the aerosolized spray comprises aerosolized droplets having a mean size in the range from about 3 μm to about 8 μm.

11. An insulin formulation as in claim 1, wherein less than 3% of the formulation is converted to foam during aerosolization.

* * * * *